(12) United States Patent
Clement et al.

(10) Patent No.: US 8,853,245 B2
(45) Date of Patent: Oct. 7, 2014

(54) ORALLY BIOAVAILABLE DABIGATRAN PRODRUGS FOR THE TREATMENT OF DISEASES

(75) Inventors: Bernd Clement, Kiel (DE); Joscha Kotthaus, Kiel (DE); Juerke Kotthaus, Kiel (DE); Dennis Schade, La Jolla, CA (US)

(73) Assignee: Dritte Patentportfolio Beteiligungsgesellschaft mbH & Co. KG, Schöfeld/Waltersdorf (DE)

( * ) Notice: Subject to any disclaimer, the term of this patent is extended or adjusted under 35 U.S.C. 154(b) by 0 days.

(21) Appl. No.: 13/556,612

(22) Filed: Jul. 24, 2012

(65) Prior Publication Data

US 2013/0030023 A1 Jan. 31, 2013

(30) Foreign Application Priority Data

Jul. 25, 2011 (EP) .................................. 11175230

(51) Int. Cl.
*C07D 401/12* (2006.01)
*A61K 31/4439* (2006.01)
*A61K 9/10* (2006.01)
*A61K 9/00* (2006.01)
*A61K 45/06* (2006.01)

(52) U.S. Cl.
CPC ............... *C07D 401/12* (2013.01); *A61K 9/10* (2013.01); *A61K 9/0019* (2013.01); *A61K 45/06* (2013.01); *A61K 9/0095* (2013.01)
USPC ........................................ 514/338; 546/273.4

(58) Field of Classification Search
None
See application file for complete search history.

(56) References Cited

U.S. PATENT DOCUMENTS 6,900,229 B2    5/2005  Hauel et al.
2011/0028756 A1*  2/2011  Clement et al. ............... 562/440

FOREIGN PATENT DOCUMENTS

| DE | 102008007381 A1 | 8/2009 |
| WO | 2004014894 A1 | 2/2004 |
| WO | 2005023249 A1 | 3/2005 |
| WO | WO 2008/009639 A2 * | 1/2008 |
| WO | 2009095499 A1 | 8/2009 |
| WO | 2010055022 A1 | 5/2010 |

OTHER PUBLICATIONS

West, Anthony R., Solid State Chemistry and its Applications, Wiley, New York, 1988, pp. 358 & 365.*
Search Report issued Oct. 7, 2011 in EP Application No. 11175230.9.
Holmes, "Dabigatran etexilate for the prevention of venous thromboembolism in patients undergoing elective hip and knee surgery: a single technology appriaisal," Health Technology Assessment, vol. 13, Suppl. 2, pp. 55-62 (2009).
Schirmer et al, "Novel Anticoagulants for Stroke Prevention in Atrial Fibrillation," Journal of the American College of Cardiology, vol. 56, No. 25, pp. 2067-2076 (2010).
Weber et al, "Prevention of cardioembolic stroke in patients with atrial fibrillation," Expert Review of Cardiovascular Therapy, vol. 8, No. 10, pp. 1405-1415 (2010).
Weitz, "Potential of new anticoagulants in patients with cancer," Thrombosis Research, vol. 125, Suppl. 2, pp. S30-S35 (2010).
Plumb et al, "Cost Effectiveness of Venous Thromboembolism Pharmacological Prophylaxis in Total Hip and Knee Replacement: A Systematic Review," Pharmacoeconomics, vol. 28, No. 9, pp. 781-785 (2010).
Fact Sheet for Pradaxa 110 mg Hard Capsules, Boehringer Ingelheim, 14 pages (Jul. 2012).
Clement, "Reduction of N-Hydroxylated Compounds: Amidoximes (N-Hydroxyamidines) as Pro-Drugs of Amidines," Drug Metabolism Reviews, vol. 34, No. 3, pp. 565-579 (2002).
Havemeyer et al, "Identification of the Missing Component in the Mitochondrial Benzamidoxime Prodrug-converting System as a Novel Molybdenum Enzyme", Journal of Biological Chemistry, vol. 281, No. 46, pp. 34796-34802 (2006).
Gruenewald et al, "The Fourth Molybdenum Containing Enzyme mARC: Cloning and Involvement in the Activation of N-Hydroxylated Prodrugs", Journal of Medicinal Chemistry, vol. 51, pp. 8173-8177 (2008).
Stangier et al, "The pharmacokinetics, pharmacodynamics and tolerability of dabigatran etexilate, a new oral direct thrombin inhibitor, in healthy male subjects," British Journal of Clinical Pharmacology, vol. 64, No. 3, pp. 292-303 (2007).
Rolan, "Plasma protein binding displacement interactions—why are they still regarded as clinically important?" British Journal of Clinical Pharmacology, vol. 37, pp. 125-128 (1994).
Int'l Preliminary Report on Patentability issued Feb. 6, 2014 in Int'l Application No. PCT/EP2012/063071.

* cited by examiner

*Primary Examiner* — Zinna Northington Davis
(74) *Attorney, Agent, or Firm* — Panitch Schwarze Belisario & Nadel LLP

(57) ABSTRACT

The present invention relates to prodrug derivatives of dabigatran, their use in the treatment and/or prophylaxis of diseases, in particular thrombotic diseases, stroke, cardiac infarction and/or atrial fibrillation and cardiac arrhythmia, as well as oncological diseases of any pathogenesis.

12 Claims, 5 Drawing Sheets

ORALLY BIOAVAILABLE DABIGATRAN PRODRUGS FOR THE TREATMENT OF DISEASES

BACKGROUND OF THE INVENTION

The present invention relates to prodrug derivatives of dabigatran, their use for the treatment and/or prophylaxis of diseases, in particular thrombotic diseases, stroke, cardiac infarction and/or atrial fibrillation and cardiac arrhythmia, as well as oncological diseases of any pathogenesis.

Within the last few years, dabigatran etexilate (Pradaxa®) has been established in thrombosis prevention after hip and knee replacement surgeries. In addition, this active agent was approved for further fields of indication (atrial fibrillation, stroke prevention and secondary prevention after heart attack, acute coronary syndrome). In the long run, further promising fields of indication are also conceivable, in particular in the cardiovascular field, as well for cancer therapy. Despite its successful market launch, dabigatran etexilate also has unfavorable substance properties which can limit its wide use.

Thus, dabigatran etexilate, i.e., a prodrug of the actual active substance dabigatran, for example, is of very poor solubility, which results in some disadvantages both in the usage as well as preparation of the medicinal product. To improve the solubility of the compound, the medicinal substance is applied onto pellets containing tartaric acid which is very cost-intensive due to a considerable technical expenditure for preparing this galenic form. Moreover, the bioavailability is adversely affected by the poor solubility of the compound so that the medication consists of two capsules, which in turn negatively influences patient compliance.

BRIEF SUMMARY OF THE INVENTION

The goal of the present invention was to develop prodrugs of dabigatran which, apart from a sufficient oral bioavailability, also have improved substance properties such as, for instance, improved solubility. Various dabigatran derivatives were synthesized for this purpose. By the N-hydroxylation of the amidine function of dabigatran, dabigatran was converted into dabigatran amidoxime (2), resulting in reduced basicity and enhanced absorption from the gastrointestinal tract. In addition, reference was made within our studies to the "coupling of amidoximes to dicarboxylic acids" prodrug principle, as described in WO2009095499 and DE102008007381. This prodrug principle was transferred to dabigatran and the obtained compounds were characterized in detail and examined with respect to their bioavailability.

The active agent dabigatran is a highly potent thrombin inhibitor which is not available orally. For this reason, the compound is used at present as an etexilate prodrug (dabigatran etexilate, Pradaxa®). Although the compound is orally available and of good action, the compound possesses considerable negative properties, described above, due to application of the prodrug principle. In the light of the above, the present invention was based on the task of providing dabigatran prodrugs which exhibit improved properties as compared to the known pharmaceutical forms of dabigatran. Said task is solved according to the invention by a compound of formula (I):

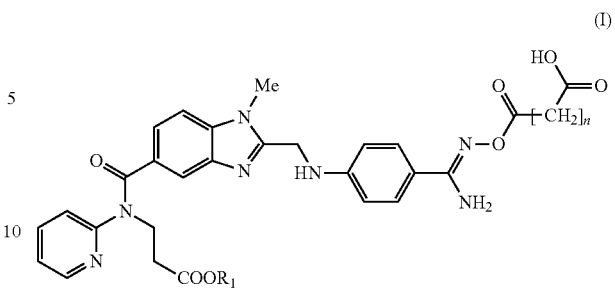

In formula (I), R represents hydrogen or a branched or unbranched, saturated or unsaturated, substituted or non-substituted hydrocarbon chain having a chain length of 1 to 12, and n represents 1-10. The invention also relates to pharmaceutically acceptable derivatives of the formula (I) compound.

In a preferred embodiment, n represents 2 in formula (I).

In another preferred embodiment, $R^1$ represents ethyl in formula (I).

In a particularly preferred embodiment, the compound according to the invention is dabigatran amidoxime succinic acid ester (1). In comparative studies with other dabigatran prodrugs, the dabigatran amidoxime succinic acid ester (1) proved to be an advantageous dabigatran prodrug which possesses excellent solubility, appropriate stability, and good oral bioavailability. Moreover, the prodrug is easily converted into the active form dabigatran. Activation ensues by means of esterases as well as a molybdenum-containing enzyme system (mARC), and is hence independent of cytochrome P450 enzymes which would involve the risk of interactions.

The present invention furthermore relates to salts, solvates, and solvates of the salts of the cited formula (I) compounds.

The present invention furthermore relates to the cited formula (I) compounds for the treatment and/or prophylaxis of diseases.

In a preferred embodiment, the present invention relates to the cited compounds for use in the treatment and/or prophylaxis of thrombotic diseases.

In a further preferred embodiment, the present invention relates to the cited formula (I) compounds for use in the treatment and/or prophylaxis of thrombotic events, e.g. venous thromboembolism (VTE).

In a further preferred embodiment, the present invention relates to the cited formula (I) compounds for use in the treatment and/or prophylaxis of stroke, cardiac infarction and/or atrial fibrillation and cardiac arrhythmia.

In a further preferred embodiment, the present invention relates to the cited formula (I) compounds for use in the treatment and/or prophylaxis of oncological diseases of any pathogenesis.

The present invention also relates to a drug comprising at least one of the cited formula (I) compounds having a prolonging effect on thrombin time, a thrombin inhibiting effect and/or an inhibiting effect on related serine proteases.

Further, the present invention also relates to a drug comprising at least one of the cited formula (I) compounds, if appropriate in combination with an inert, non-toxic, pharmaceutically suited excipient.

The present invention furthermore also relates to a drug comprising at least one of the cited formula (I) compounds in combination with a further active agent.

The present invention furthermore also relates to a drug for oral or parenteral administration.

The present invention also further relates to a drug as described above which is of enteric formulation. In addition, the present invention relates to a method for the treatment and/or prophylaxis of thrombotic diseases, stroke, cardiac infarction and/or atrial fibrillation and cardiac arrhythmia in humans or animals using at least one of the cited formula (I) compounds or one of the cited drugs.

Further, the present invention relates to a method for the treatment and/or prophylaxis of oncological diseases in humans or animals using at least one of the cited formula (I) compounds or one of the cited drugs.

The present invention also relates to a method for preparing the inventive compound having formula (I)

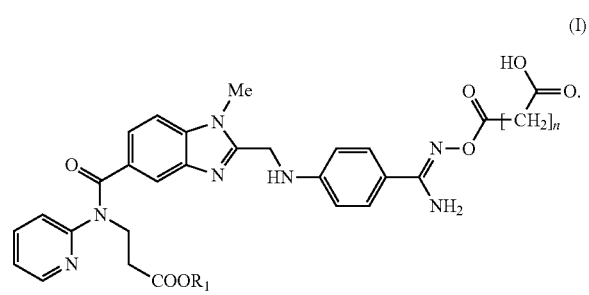

The method involves converting a nitrile of formula (A):

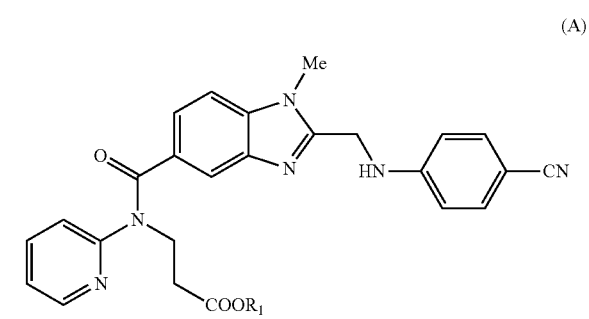

in which $R_1$ represents hydrogen or a branched or unbranched, saturated or unsaturated, substituted or non-substituted hydrocarbon chain having a chain length of 1 to 12, into an amidoxime of formula (B)

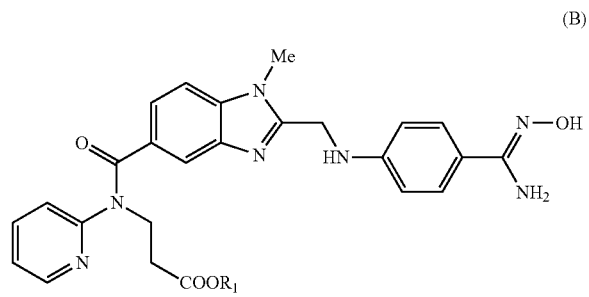

and reacting the amidoxime (B) with a dicarboxylic acid anhydride of the formula (C),

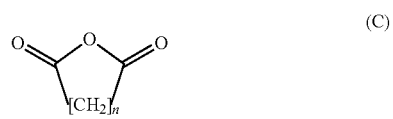

in which n represents 1-10, to yield the compound having formula (I).

The present invention deals with the development of novel dabigatran prodrugs having improved properties as compared to dabigatran etexilate. Within our systematic developing and subsequent characterizing of the novel prodrugs, dabigatran amidoxime succinic acid ester (1) proved to be an extraordinarily suited prodrug. This prodrug is characterized by excellent properties such as good solubility, fast activation, and oral bioavailability comparable to that of dabigatran etexilate. The decisive advantage of this prodrug resides in its improved substance properties: Due to the considerably increased solubility, the complicated pharmaceutical formulation which is required with Pradaxa® may be dispensed with, leading among other things to a considerable reduction of manufacturing costs. Moreover, another galenic formulation allows the required active dosage of the dabigatran amidoxime succinic acid ester (1) to be orally administered in one tablet or capsule which can result in a considerable improvement in patient compliance. In addition, parenteral applications (injections, infusions, etc.) of the compound are also conceivable due to the good solubility of the prodrug, which are not possible when using Pradaxa®.

A further aspect able to be improved by the prodrug described herein is reducing the side effects described with dabigatran etexilate, in particular the occurrence of gastrointestinal bleeding.

In summary, a prodrug of dabigatran may be obtained by applying the general prodrug principle as described in WO2009095499 or DE102008007381, which shows a considerable improvement over the hitherto known medicinal substance dabigatran etexilate. When dabigatran amidoxime succinic acid ester (1) is used, the manufacturing costs can be drastically reduced on the one hand, and the clinical application decisively optimized on the other.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Synthesis

Figure 1:
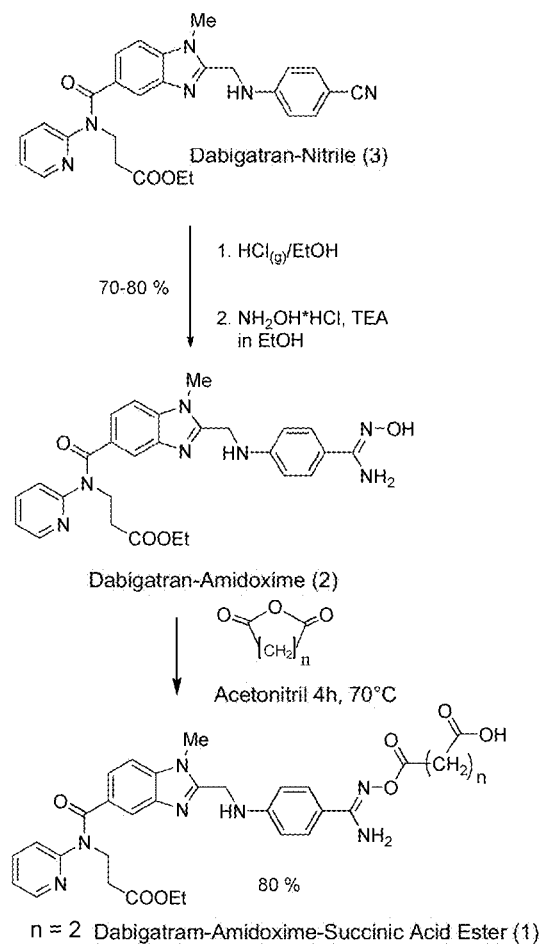
FIG. 1 is a schematic view of the synthesis of the dabigatran prodrug according to the invention.

The dabigatran amidoxime succinic acid ester (1) was prepared starting from dabigatran nitrile (3) via the dabigatran amidoxime (2) as shown in FIG. 1. The dabigatran amidoxime (2) is suspended in dried MeCN and reacted with the corresponding acid anhydride (succinic acid anhydride, etc.). The substance could be isolated by subsequently adding diethyl ether and directly filtering off.

Stability

Figure 2:
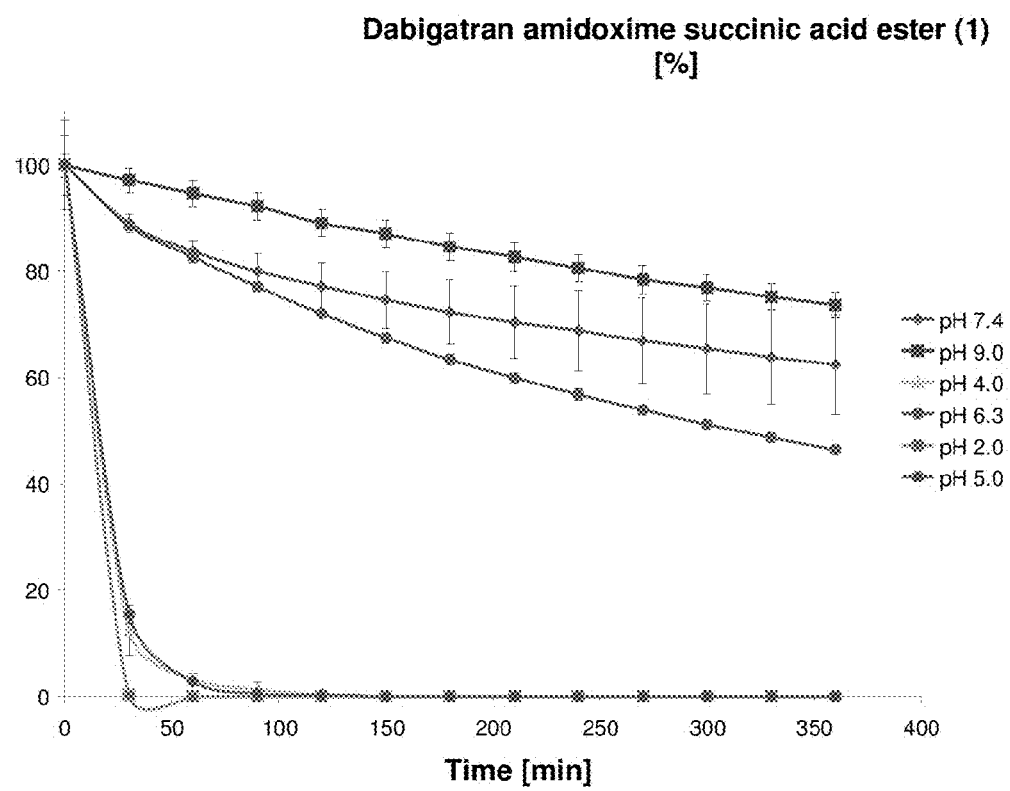
FIG. 2 depicts the stability of the dabigatran amidoxime succinic acid ester (1) at various pH values.

Stability analysis showed that the dabigatran amidoxime succinic acid ester (1) is rather instable in acidic medium (<pH 6) (FIG. 2). The succinyl ester bond is completely cleaved so that the dabigatran amidoxime (2) forms. The compound is clearly more stable in the neutral or light alkaline pH range. In the examined period of 360 min, succinyl ester cleavage of about 25% was determined at a pH value of 9.0, and about 40% at a pH value of 7.4. It follows from these data that the compound should be enterically formulated for later use as a medicinal substance so as to withstand the stomach passage unaltered and hence can be completely resorbed in the upper intestinal regions.

Figure 3:
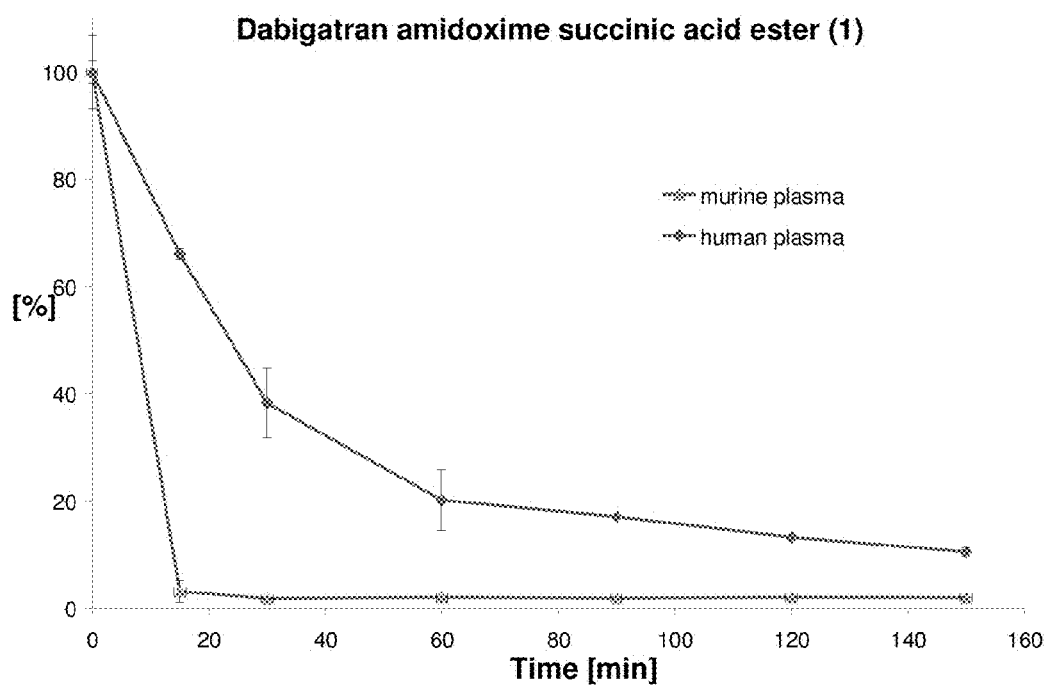
FIG. 3 depicts the stability of the dabigatran amidoxime succinic acid ester (1) in murine and human plasma.

As expected, incubations in human and murine plasma showed a pronounced hydrolysis of the ester bond (FIG. 3). This hydrolysis in the plasma is desired since it leads to the activation of the prodrug and hence to the release of the dabigatran active agent. It is catalyzed by esterases which are ubiquitously present in plasma.

Solubility

Dabigatran amidoxime succinic acid ester (1) has a very good solubility in the 6.3 to 9.0 pH range analyzed (see Table 1). The solubility in acidic medium (pH 2.0) could not be precisely characterized due to the above-described hydrolysis. Preliminary test runs, however, showed good solubility here as well.

Table 1 shows the solubility of dabigatran amidoxime succinic acid ester (1) compared to other dabigatran prodrugs. Here, the comparison with dabigatran etexilate should be particularly emphasized. The data obtained make it clear that the solubility of the newly developed dabigatran prodrug (1) had been drastically improved. As compared to the etexilate prodrug, the solubility is thus improved between 1000 and 100,000 times depending on the pH value, which favors its use in medicinal products. In addition, the good solubility of the dabigatran amidoxime succinic acid ester (1) also allows for the conceiving of parenteral forms of administration such as, for instance, injections and infusions.

Protein Binding

The analyses of plasma protein binding showed that compound (I), at a plasma protein binding of about 22%, exhibits very low levels of protein binding. Only from a value of about 90% on are protein bonds to be classified as being critical with respect to their potential of interaction. Dabigatran amidoxime succinic acid ester (1) can thus be classified as being non-critical in this respect.

Prodrug Concept

The prodrug concept itself was described in WO2009095499 and DE102008007381 by other exemplary embodiments. The concept was transferred to dabigatran in this study. This newly developed dabigatran amidoxime succinic acid ester (1) has now proven—after a profound characterization in both in vitro and in vivo studies—to be a very suitable dabigatran prodrug for developing medicinal products. The prodrug is activated by means of esterases and the mARC enzyme system and is hence independent of cytochrome P450 enzymes. The participation of P450 enzymes always involves the risk of interactions, which are not described in our selected activation mechanism.

In Vitro Activation

The in vitro activation studies conducted showed the excellent extent of dabigatran amidoxime succinic acid ester (1) activation (see Table 2).

The incubations in human and murine plasma already showed very marked ester cleavage, which is necessary for activating the prodrug (FIG. 3).

The subsequent reduction to dabigatran could also be detected in the incubations with subcellular enzyme preparations (Table 2). The conversion rates identified in incubations with porcine enzyme sources showed that the dabigatran amidoxime succinic acid ester (1) is excellently converted into the active form. As expected, the reduction from amidoxime to amidine ensued faster in microsomes and mitochondria preparations than in 9000×g fractions.

It can be stated in summary that the dabigatran amidoxime succinic acid ester (1) is a very suitable prodrug of dabigatran. Both the ester cleavage and the reduction proceed to an extent that allows therapeutically active plasma levels of dabigatran to develop.

Oral Bioavailability

Figure 7:
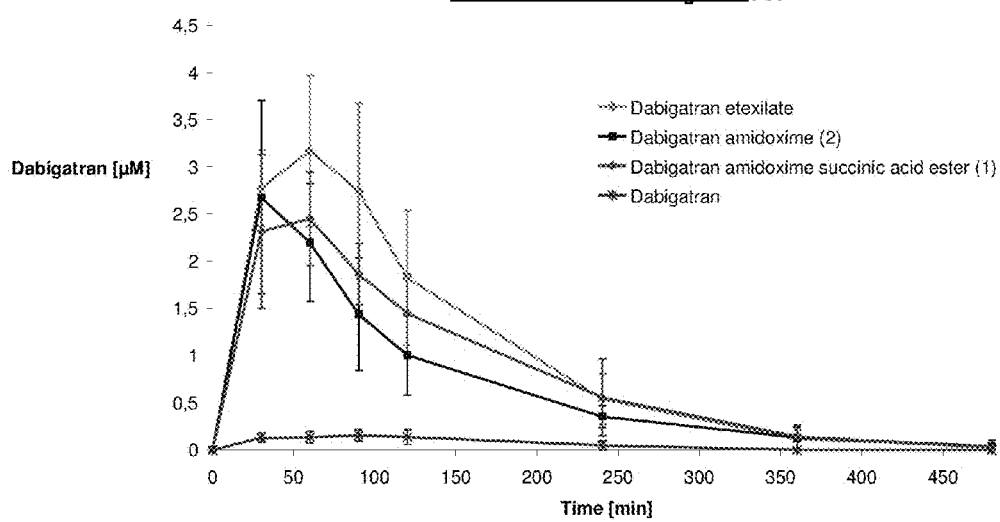
FIG. 7 is a summary of the plasma levels of dabigatran after oral administration of various dabigatran prodrugs (50 mg/kg). Shown are the mean plasma concentration values.

The oral bioavailability of dabigatran amidoxime succinic acid ester (1) is demonstrated in the animal studies conducted. After orally administering the prodrug, dabigatran plasma levels could be measured over a period of 480 min, which are comparable to those after oral administration of dabigatran etexilate (FIG. 7, Table 3). No further metabolites could be detected apart from the dabigatran active form, which is indicative of the rapid and complete activation of the prodrugs. The oral bioavailability of the dabigatran amidoxime succinic acid ester (1) was detected to be 5.5%±1.7%. The maximum plasma concentrations were in the range of from 1.8 to 3.7 μM and were obtained 30-60 min after the oral administration. The determined bioavailability of the dabigatran amidoxime succinic acid ester (1) does not differ significantly from the results obtained after oral administration of dabigatran etexilate. The developing of the dabigatran amidoxime succinic acid ester (1) has thus succeeded in developing a prodrug comparable to the dabigatran etexilate in terms of bioavailability.

Figure 8:
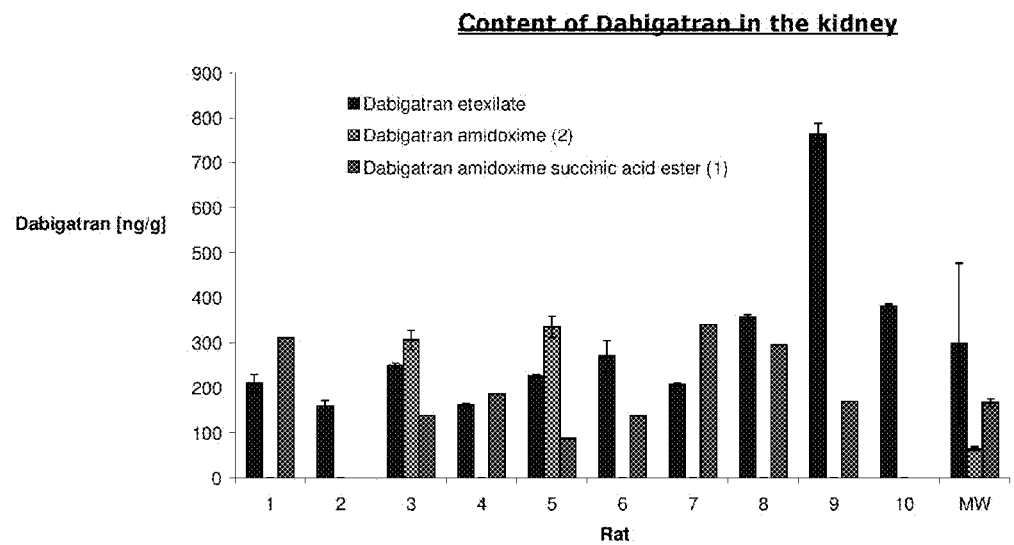
FIG. 8 is a summary of the concentration [ng/g] of dabigatran in the kidney after oral administration of the various prodrugs (50 mg/kg). Shown are the concentrations of the kidneys of all of the tested rats.
Figure 9:
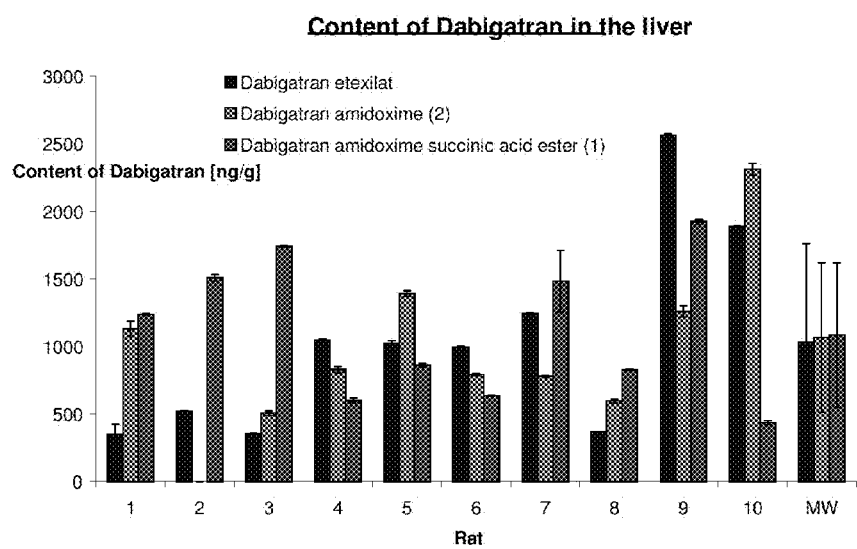
FIG. 9 is a summary of the concentration [ng/g] of dabigatran in the liver after oral administration of the various prodrugs (50 mg/kg). Shown are the concentrations of the livers of all of the tested rats.

The analysis of organ samples (kidney and liver) showed that small amounts of dabigatran can be detected both in the liver and kidney after oral administration of the dabigatran amidoxime succinic acid ester (1) (FIGS. 8 and 9).

The newly developed prodrugs are orally bioavailable prodrugs of dabigatran. By converting the dabigatran into the prodrugs according to the invention, important substance properties could be considerably optimized. To be mentioned in particular is the drastically improved solubility of the dabigatran amidoxime succinic acid ester (1), resulting in various advantages in manufacturing and administering the medicinal substance. Thus, the improved solubility allows dispensing with complicated galenic and cost-intensive formulations. Presently, dabigatran etexilate is marketed as a capsule with tartaric acid-containing pellets (Pradaxa®). Using the dabigatran amidoxime succinic acid ester (1) allows dispensing with such technically demanding methods. In addition, the administration and hence patient compliance can be optimized in that only one capsule/tablet must be swallowed instead of the usual two capsules required for Pradaxa®.

Except for the acidic pH range, the compound possesses a good chemical stability. The marked hydrolysis in acidic medium is a condition that the prodrug should be administered as an enteric formulation when administered orally so as to preclude premature hydrolysis in the stomach.

The in vitro bioactivation assays evidenced a rapid and extensive activation of the prodrug into dabigatran. The activation proceeds independently of cytochrome P450 enzymes and hence does not involve the risk of interactions.

The good oral bioavailability was also proven experimentally in the subsequent animal studies conducted. The oral bioavailability of 5.5%±1.7% in this case does not differ significantly from the dabigatran etexilate reference compound.

In summary, the dabigatran amidoxime dicarboxylic acid derivatives are excellent prodrugs which dispose of excellent physicochemical parameters and possess good oral bioavailability. Comparing all of the analyzed properties, the dabigatran prodrugs according to the invention are clearly superior to dabigatran etexilate.

Material and Methods

Exemplary Embodiments

Synthesis of Ethyl-3-({2-[(4-(N'-(3-carboxypropanoyloxy)amidino)phenylamino)methyl]-1-methyl-1H-benzimidazol-5-carbonyl}pyridine-2-yl)propionate (1) (Dabigatran amidoxime succinic acid ester)

(I)

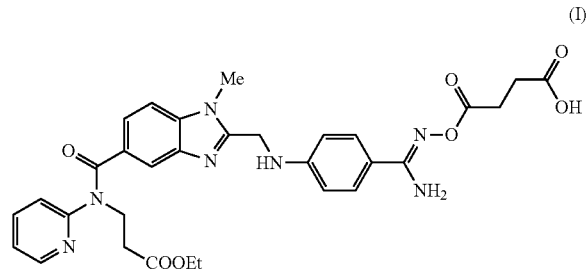 [SMILES: CCOC(=O)CCN(C(=O)c1ccc2c(c1)nc(CNc1ccc(/C(N)=N/OC(=O)CCC(=O)O)cc1)n2C)c1ccccn1]

Dabigatran amidoxime 2 (100 mg, 0.194 mmole) was suspended in about 8 ml of dried MeCN under argon atmosphere. Succinic anhydride (20.38 mg, 0.204 mmole) was added and the mixture stirred for 4 h at about 70° C. (oil bath adjusted to 80° C.). The flask was subsequently cooled with ice and about 10 ml of diethyl ether (Et$_2$O) was added. The precipitate was filtered and thoroughly rinsed with Et$_2$O. Yield: 95 mg (80%)

$^1$H NMR (DMSO-d$_6$):

δ/ppm (TMS)=1.13 (t, $^3$J=7.1 Hz, 3H), 2.53, 2.66, 2.69 (3×t, 6H), 3.77 (s, 3H), 3.98 (q, $^3$J=7.1 Hz, 2H), 4.23 (br t, 2H), 4.55 (m$_c$, 2H), 6.44 (br s, 2H), 6.62 (br t, 1H), 6.75 (br d, $^3$J=8.5 Hz, 2H), 6.88 (m$_c$, 1H), 7.13 (m$_c$, 2H), 7.39 (br d, $^3$J=8.4 Hz, 1H), 7.47 (m$_c$, 3H), 7.54 (br t, 1H), 8.39 (m, 1H), 12.22 (br s, 1H)

$^{13}$C-NMR (DMSO-d$_6$):

δ/ppm (TMS)=13.9 (OCH$_2$CH$_3$), 28.0 (CH$_2$), 28.8 (CH$_2$), 29.8 (NCH$_3$), 33.0 (CH$_2$), 40.1, 44.3 (2×CH$_2$), 60.0 (OCH$_2$CH$_3$), 109.4 (ArCH), 111.6 (2×ArCH), 118.9 (ArC), 119.5 (ArCH), 121.2 (ArCH), 122.0 (ArCH), 122.7 (ArCH), 127.5 (2×ArCH), 129.3 (ArC), 137.2 (ArC), 137.8 (ArCH), 140.8 (ArC), 148.6 (ArCH), 150.0 (ArC), 153.9 (ArC=N), 156.0 (ArC=N), 156.6 (C=NO), 170.3 (CON), 171.0 (2×COOR), 173.6 (COOH)

HRMS (ESI) m/z:

calculated C$_{31}$H$_{33}$N$_7$O$_7$ [M+H]$^+$ 616.25142. found 616.25193

Elementary analysis C$_{31}$H$_{33}$N$_7$O$_7$ (molecular mass 615.65):

calculated: C, 60.48; H, 5.40; N, 15.93. found: C, 60.16; H, 5.24; N, 15.87.

Characterization of the Dabigatran Prodrugs

Stability Analyses of the Dabigatran Amidoxime Succinic Acid Ester (1)

A 0.2 mM solution of dabigatran amidoxime succinic acid ester (1) was prepared in 50 mM of a potassium phosphate buffer for the stability analyses. The examination took place at pH values of 2.0, 4.0, 6.3, 7.4 and 9.0. One sample was taken and immediately analyzed by HPLC every 30 min over a period of 360 min.

Further analyses were conducted with human and murine plasma. 900 μl of the plasma was mixed with 100 μl of a 2 mM solution of dabigatran amidoxime succinic acid ester (1). The final concentration of dabigatran amidoxime succinic acid ester (1) was thus 0.2 mM. The samples were incubated at 37° C. in a shaking water bath and samples were taken after 0, 15, 30, 45, 60, 90, 120 and 150 min. For this purpose, 100 μl was drawn in each case and mixed with 100 μl acetonitrile. The samples were shaken, centrifuged for 5 min and the supernatant was measured via HPLC. The results are illustrated in FIGS. 2 and 3.

Solubility of the Dabigatran Amidoxime Succinic Acid Ester (1)

An amount of the dabigatran amidoxime succinic acid ester (1) which is insoluble in 150 μl was dissolved in 50 mM of a phosphate buffer (pH 6.3, pH 7.4, respectively pH 9.0) and shaken for 10 min. Solubility was not determined at the 4.0 and 2.0 pH values due to the rapid hydrolysis of the succinyl ester at acidic pH values. 3 N HCl, respectively 10% KOH, was used to adjust the pH value. After the 10 min period, the undissolved portion was removed by centrifugation (13,000 RPM, 10 min) and the samples were immediately measured by HPLC. The evaluation of the solubility ensued via a calibration of dabigatran amidoxime succinic acid ester (1) (Table 1).

Dabigatran etexilate and dabigatran amidoxime (2) were examined by comparison so as to be able to better judge the solubility as compared to previously described derivatives. Solubilities were determined analogously to the method described for compound (1).

TABLE 1

Solubility of the dabigatran amidoxime succinic acid ester (1) and other dabigatran prodrugs at various pH values

| Dabigatran prodrug | solubility [μM] | | |
|---|---|---|---|
| | pH 6.3 | pH 7.4 | pH 9.0 |
| Dabigatran amidoxime succinic acid ester (1) | 630 ± 290 μM | 4620 ± 830 μM | 8160 ± 440 μM |
| Dabigatran amidoxime (2) | 145 ± 16 μM | 119 ± 5 μM | 111 ± 8 μM |
| Dabigatran etexilate | 3.6 ± 2.0 μM | 0.6 ± 0.4 μM | 0.4 ± 0.1 μM |

Determination of the Protein Binding of the Dabigatran Amidoxime Succinic Acid Ester (1)

The plasma protein binding was determined at three different concentrations (10, 25, and 50 μM). A 4% albumin solution was used as the protein solutions. 50 μl of a 10 times concentrated substance solution were in each case pipetted to 450 μl of the protein solution. Incubation ensued over 15 min in a shaking water bath at 37° C. Subsequently, the samples were transferred into ultrafiltration units (Vivaspin 500, 10 kDa cut off) and centrifuged for 15 min at 10,000 RPM. The filtrate was analyzed by HPLC. Additionally, a control which was not mixed with protein nor centrifuged was carried out for each concentration. A further control without protein addition which, however, was centrifuged by the filtration unit served to validate the methodology.

The analysis of the sample identified a protein binding of 21.8±5.3% for the dabigatran amidoxime succinic acid ester (1). Analogous analyses rendered values of 31.2±1.3% for the dabigatran amidoxime (2).

Analysis of the Dabigatran Amidoxime Succinic Acid Ester (1) Bioactivation

Ascertaining Prodrug Activation Using Various Subcellular Enzyme Systems

The activation of the prodrug was determined in vitro by means of subcellular enzyme preparations. 9000×g of supernatants, microsomes, and mitochondria of porcine liver and kidney tissues were used as the enzyme preparations. The incubation batches were composed of 500 mM prodrug, 1 mM NADH, 1 U esterase and 0.3 mg enzyme preparation dissolved in 250 μl 100 mM phosphate buffer, pH 6.3. The incubation took place over 30 min in a shaking water bath at 37° C. The incubation was terminated by adding 250 μl of methanol. The samples were subsequently shaken for 20 min and the precipitated protein was removed by centrifuging at 10,000 RPM for 15 min. The supernatant was measured by HPLC. The identified conversion rates are indicated in table 2.

TABLE 2

Activation of the dabigatran amidoxime succinic acid ester (1) into the active form using subcellular enzyme preparations

| Enzyme source | Dabigatran [nmol * min$^{-1}$ * mg$^{-1}$] |
|---|---|
| SN 9000 g | 7.1 ± 0.9 |
| SN Ms | 13.6 ± 1.1 |
| SL 9000 g | 8.3 ± 0.5 |
| SL Ms | 18.2 ± 0.5 |
| SL Mt | 15.9 ± 0.9 |

SL = pig liver,
SN = pig kidney,
9000 g = 9000 g supernatant,
MS = microsomes,
Mt = mitochondria HPLC Analytics:

The following HPLC analytics were used in evaluating:

Identification of Succinyl Dabigatran:

| | |
|---|---|
| HPLC system | Waters Autosampler 717plus, Waters 600 Controller, Waters 600 Pump, Waters 2487 Dual λ Absorbance Detector and EZChrom Elite Client/Server imaging and evaluation software (Version 2.8.3) |
| Stationary phase | LiChroCart, LiChrospher 60 RP-select B (VDS Optilab, length 125 * 4 mm, particle size 5 μm) with 4 * 4 mm precolumn (Merck) |
| Mobile phase | A  50%  methanol<br>B  50%  aqua bidest with 0.1% TFA<br>20 mM K$_2$HPO$_4$ pH 6.5 |
| Detection | 293 nm |
| Flow rate | 1.0 ml/min |
| Run time | 7.5 min |
| Injection volume | 15 μl |
| Retention time | Dabigatran amidoxime succinic acid ester (1): 2.1 ± 0.1 min<br>Dabigatran amidoxime (2): 3.8 ± 0.1 min |

Identification of Dabigatran:

| | |
|---|---|
| HPLC system | Waters Autosampler 717plus, Waters 600 Controller, Waters 600 Pump, Waters 2487 Dual λ Absorbance Detector and EZChrom Elite Client/Server imaging and evaluation software (Version 2.8.3) |
| Stationary phase | LiChroCart, LiChrospher 60 RP-select B (VDS Optilab, length 125 * 4 mm, particle size 5 μm) with 4 * 4 mm precolumn (Merck) |
| Mobile phase | A  30%  methanol<br>B  70%  aqua bidest with 0.1% TFA<br>20 mM K$_2$HPO$_4$ pH 4.3 |
| Detection | 293 nm |
| Flow rate | 1.0 ml/min |
| Run time | 7.5 min |
| Injection volume | 20 μl |
| Retention time | Dabigatran Amidoxime (2): 4.1 ± 0.1 min<br>Dabigatran: 4.5 ± 0.1 min |

Oral Bioavailability (Animal Study)

Dabigatran was administered intravenously to 20 rats in a concentration of 10 mg/kg. Dabigatran amidoxime succinic acid ester (1), dabigatran amidoxime (2), and dabigatran etexilate were administered to 10 rats each in a concentration of 50 mg/kg as a suspension with Arabic gum (10% m/V) per gavage. 100 mM of potassium phosphate buffer of pH 9.0 was used with the dabigatran amidoxime succinic acid ester (1) in preparing the suspension so as to prevent premature cleavage of the succinyl ester in the acidic environment of the stomach. In addition, 3 rats were given dabigatran at a dosage of 50 mg/kg per gavage in order to determine the oral bioavailability of the active form itself.

After the intravenous administration, plasma samples were taken after 5, 10, 25, 50, 100, 200, and 400 min, respectively 30, 60, 90, 120, 240, 360, and 480 min after oral administration. For this purpose, 300 µl of whole blood was drawn using an insulin syringe and transferred into EDTA-coated CB 300 microvettes (Sarstedt, Nümbrecht). After each withdrawal, the sample was rinsed with 100 µl of 0.9% saline solution respectively with heparin solution (250 I.E./ml) at an interval of 60 min. The blood sample was briefly shaken and placed on ice until centrifugation (4° C.; 14,000 RPM; 10 min). The samples were stored further at −80° C.

Slaughter ensued by guillotine decapitation 8 hours after the drug administration. The organs were subsequently removed. All organs were cleaned and frozen in 2-methylbutane cooled in dry ice. Liver, kidney, lung, spleen, heart, and brain were removed.

Sample Preparation: Plasma Samples

The plasma samples were defrosted at room temperature. 5 µl of 1N HCl was prepared in each case and 55 µl of the plasma samples added by pipetting. The samples were subsequently shaken for 45 min in order to cleave the existing glucuronides. The plasma proteins were then precipitated with 55 µl of methanol and shaken for a further 30 min. The samples were centrifuged at 10,000 RPM for 15 min and the supernatant was transferred into HPLC vials. 10 µl was used in each case for the HPCL determinations.

Calibrations and analyses for recovering the dabigatran were performed in a phosphate buffer of pH 7.4, murine plasma respectively, so as to quantitatively evaluate the plasma samples.

Organ Samples

The organs were defrosted at room temperature and weighed. Depending on the respective organ, differing amounts of the tissues were prepared. About 1000 mg were used in case of the liver samples; about 500 mg in case of the kidney samples. Liver and kidney were examined since both organs participate in the activation of the prodrug and increased concentrations of dabigatran can therefore occur in same. Other organs are irrelevant for the bioactivation and were therefore not examined.

The organ samples (liver and kidney) were minced by means of a potter. For this purpose, each of the weighed tissues were minced with 1 ml aqua bidest for 5 min. The potter vessel was subsequently rinsed in each case with 1 ml of aqua bidest. The samples were transferred into reaction vessels and the same volume of acetonitrile was added in order to precipitate proteins. The samples were shaken for 45 min and subsequently centrifuged at 12,000 RPM for 15 min. The supernatant was transferred into glass bottles and concentrated under compressed air. The residue was washed with 500µ of acetonitrile, re-centrifuged, and the supernatant added to the remaining samples. The residue was discarded. After concentrating under compressed air, the samples were freeze-dried overnight.

The solubilizing of the samples ensued with 400 µl of a mixture of methanol/aqua bidest (50/50). The samples were shaken at room temperature for 1.5 hours and the residue subsequently removed by centrifugation (15,000 RPM, 15 min). The concentration of dabigatran was determined from the supernatant by means of HPLC.

A preparation of the organ samples after oral administration of the active agent was dispensed with since administering the active form of dabigatran only serves in determining the bioavailability.

Results of the Animal Study

Figure 4:
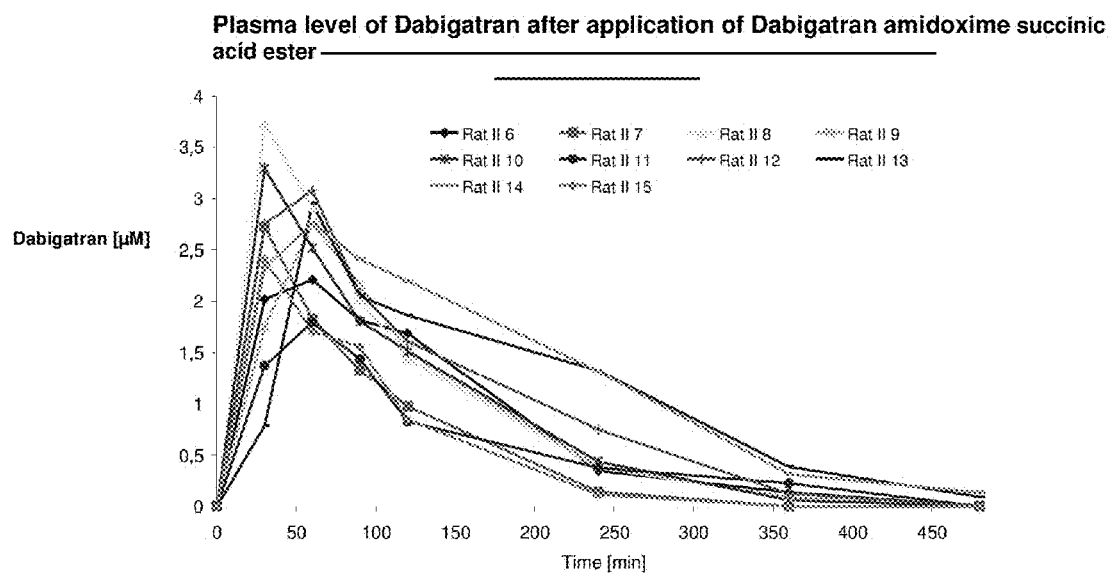
FIG. 4 shows the plasma level of dabigatran after oral administration of the dabigatran amidoxime succinic acid ester (1) (50 mg/kg). Shown are the plasma concentrations in all tested rats (n=10).
Figure 5:
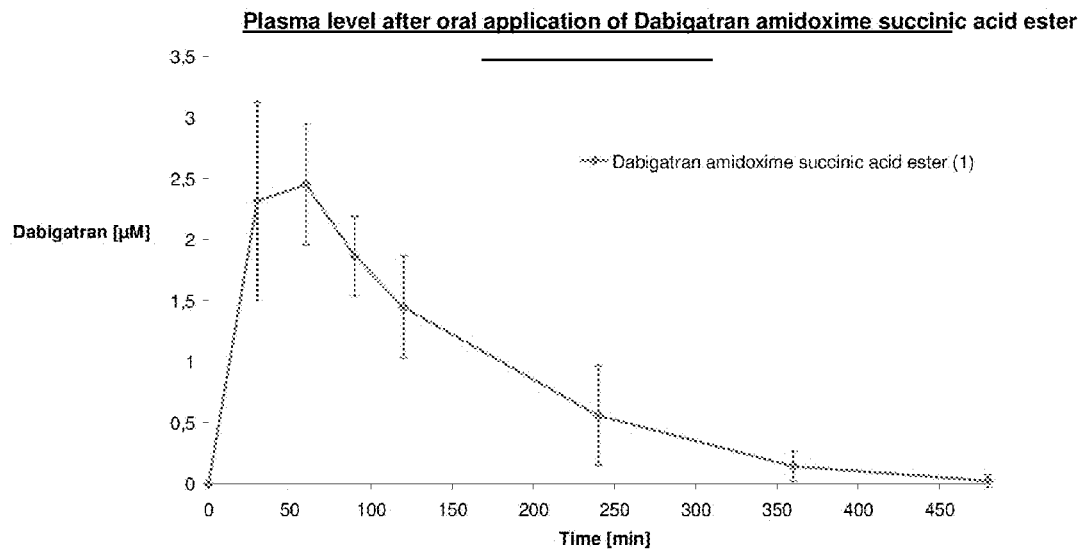
FIG. 5 shows the plasma level of dabigatran after oral administration of the dabigatran amidoxime succinic acid ester (1) (50 mg/kg). Shown are the mean plasma concentration values of dabigatran in all tested rats (n=10).

The analysis of the plasma samples after oral administration of the dabigatran amidoxime succinic acid ester (1) rendered detectable plasma levels over the entire test period of 480 min. The plasma levels obtained are illustrated in FIGS. 4 and 5.

Only the active form, the dabigatran, could be detected in the analysis of the plasma samples. The prodrug itself could not be identified in the plasma which is indicative of a very good activation of the prodrug. After oral administration of the dabigatran amidoxime succinic acid ester (1), maximum plasma concentrations between 1.8 and 3.7 µM could be determined which were reached 30-60 min after oral administration.

The analysis of the plasma samples after intravenous administration of dabigatran rendered detectable plasma levels over a period of 400 min (FIG. 6) and is used for calculating the oral bioavailability.

Figure 6:
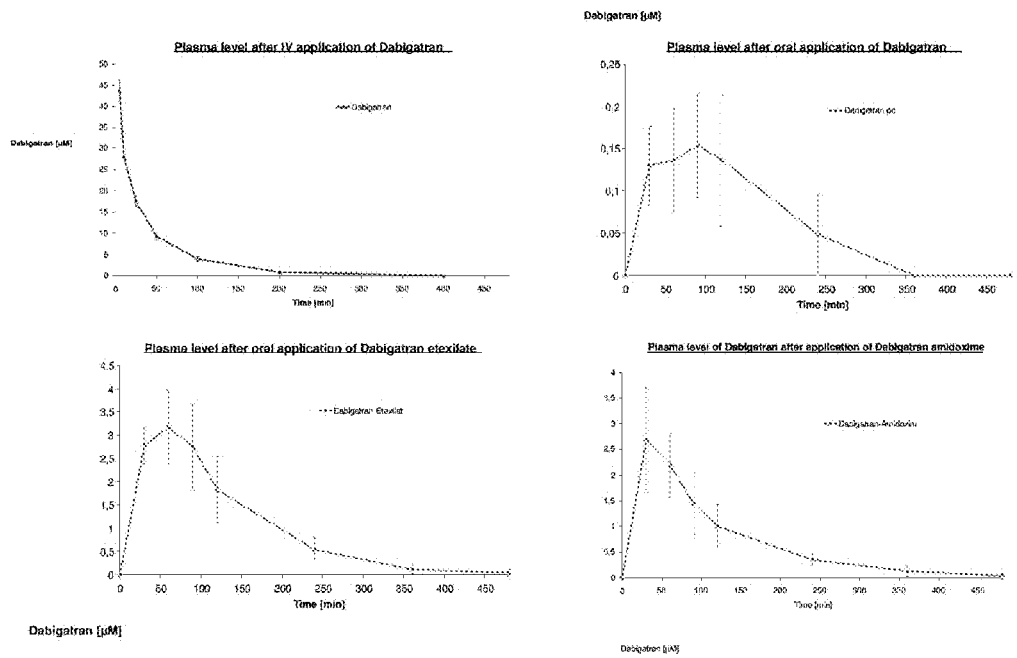
FIG. 6 shows the plasma level of dabigatran after intravenous (10 mg/kg; n=20) and oral administration of dabigatran (50 mg/kg, n=3) and oral administration of various dabigatran prodrugs (50 mg/kg, n=10). Shown are the mean plasma concentration values of dabigatran in all tested rats.

After administration of the two reference prodrugs (dabigatran amidoxime (2) and dabigatran etexilate), same could be detected over the test period of 480 min. The plasma levels obtained are illustrated in FIG. 6. In the analysis of the plasma samples, only the active form, the dabigatran, could be detected in each case. The prodrugs themselves could not be identified in the plasma. After orally administering the dabigatran etexilate, maximum plasma concentrations of between 2.3 and 4.5 µM could be determined which were reached 30-90 min after the oral administration. After orally administering the dabigatran amidoxime (2), maximum plasma concentrations of between 1.7 and 5.5 µM could be determined which were reached 30-60 min after the oral administration.

Summary and Comparison of the Three Dabigatran Prodrugs (FIG. 7):

A comparison of the results of the in vivo studies conducted with the different prodrugs (dabigatran amidoxime (2), dabigatran etexilate and dabigatran amidoxime succinic acid ester (1)) shows that the highest plasma concentrations could be determined after application of the dabigatran etexilate (7.2%±2.0%) followed by dabigatran amidoxime succinic acid ester (1) and dabigatran amidoxime (2). The bioavailability ascertained for the dabigatran etexilate in the in vivo study we conducted hence coincides with the etexilate data (5-8%) described in the literature. The bioavailability of the dabigatran amidoxime succinic acid ester (1) was determined to be 5.5%±1.7% (Table 3) and does not significantly differ from the results obtained after oral administration of the dabigatran etexilate. Dabigatran amidoxime succinic acid ester (1) is thus a prodrug comparable to dabigatran etexilate in terms of bioavailability.

Bioavailability of the Dabigatran Derivatives:

The bioavailability of the different dabigatran prodrugs was calculated by means of the PK Solutions 2.0™ program using the plasma concentrations. Furthermore, the plasma half-life $t_{1/2}$, the time of maximum plasma level $t_{max}$, as well as the maximum plasma concentration $c_{max}$ were calculated. The data obtained is illustrated in Table 3.

TABLE 3

Pharmacokinetic parameters of the dabigatran derivatives

| | $t_{max}$ [min] | $c_{max}$ [μM] | $t_{1/2}$ [min] | bioavailability [%] |
|---|---|---|---|---|
| Dabigatran amidoxime succinic acid ester (1) | 48.0 ± 15.5[+] | 2.77 ± 0.55* | 69.3 ± 30.4[+] | 5.5 ± 1.7[+,#] |
| Dabigatran amidoxime (2) | 36.0 ± 12.6* | 2.76 ± 1.06* | 108.1 ± 56.2[+] | 4.1 ± 1.4* |
| Dabigatran etexilate | 57.0 ± 22.1 | 3.48 ± 0.64 | 87.7 ± 27.5 | 7.2 ± 2.0 |
| Dabigatran | 105.0 ± 21.2* | 0.24 ± 0.13* | 58.0 ± 31.1[+] | 0.3 ± 0.2* |

*p < 0.05 (as compared to dabigatran etexilate), significant
[+]p > 0.05 (as compared to dabigatran etexilate), not significant
[#]p < 0.05 (as compared to N—OH-dabigatran), significant
n.b. = not determined (due to very high fluctuations in the terminal plasma levels)

Evaluation of the Organ Samples:

The analysis of the prepared organ samples yielded detectable concentrations of dabigatran both in the liver as well as in the examined kidneys. Comparable concentrations of dabigatran were ascertained in the liver tissues after oral administration of the etexilate, the amidoxime (2) and the succinyl ester (1). After administration of the succinyl ester, the concentration was clearly lower in all examined liver samples (see FIG. 9). The total amounts detected in liver were on average about 13 μg with all the prodrugs analyzed. Compared to the concentrations ascertained in the livers, the concentrations in the kidneys are clearly lower (see FIG. 8). The dabigatran concentrations detected in the tissues, however, are irrelevant for determining bioavailability since bioavailability is solely calculated from analyzed plasma concentrations. The liver and kidney dabigatran concentrations merely serve as additional information to be able to effectively characterize the newly developed prodrugs.

HPLC Analytics

The following HPLC analytics was used for analyzing the organ and plasma samples after intravenous administration of dabigatran:

| HPLC system | Waters Alliance ™ HPLC system with Waters e2695 XC Separations module, Waters 2998 Photodiode Array Detector and Empower ™ 2 imaging and evaluation software |
|---|---|
| Stationary phase | LiChroCart, LiChrospher 60 RP-select B (Merck, length 125 * 3 mm, particle size 5 μm) with 4 * 4 mm precolumn (Merck) |
| Mobile phase | 23% methanol 77% 20 mM $K_2HPO_4$ pH 6.5 with 0.1% TFA |
| Detection | 210-300 nm (293 nm) |
| Column temperature | 30° C. |
| Flow rate | 0.7 ml/min |
| Runtime | 9 min |
| Injection volume | 10 μl |
| Retention time | Dabigatran: 5.5 ± 0.2 min |

The following HPLC analytics was used for analyzing the organ and plasma samples after oral administration of dabigatran etexilate, dabigatran amidoxime (2) and dabigatran amidoxime succinic acid ester (1):

| HPLC system | Waters Alliance ™ HPLC system with Waters e2695 XC Separations module, Waters 2998 Photodiode Array Detector and Empower ™ 2 imaging and evaluation software |
|---|---|
| Stationary phase | LiChroCart, LiChrospher 60 RP-select B (Merck, length 125 * 3 mm, particle size 5 μm) with 4 * 4 mm precolumn (Merck) |
| Mobile phase | A methanol B 20 mM $K_2HPO_4$ pH 6.5 with 0.1% TFA |
| Gradient profile | time A [%] B [%] 0 77 23 6 77 23 9 50 50 18 50 50 20 77 23 25 77 23 |
| Detection | 210-300 nm (293 nm) |
| column temperature | 30° C. |
| Flow rate | 0.7 ml/min |
| Runtime | 25 min |
| Injection volume | 10 μl |
| Retention time | Dabigatran: 5.5 ± 0.2 min |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A compound having formula (I) or a pharmaceutically acceptable derivative thereof:

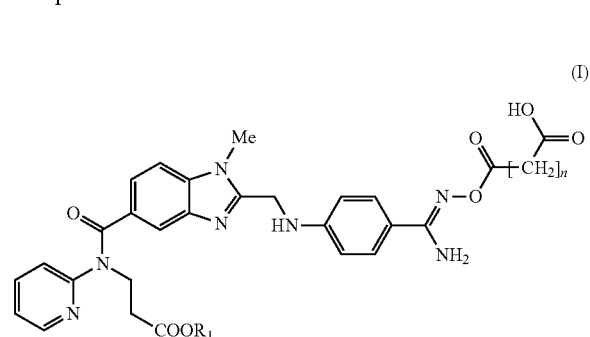

(I)

wherein $R_1$ represents hydrogen or a branched or unbranched, saturated or unsaturated, substituted or non-substituted hydrocarbon chain having a chain length of 1 to 12, and n represents 1-10.

2. The compound according to claim 1, wherein n represents 2.

3. The compound according to claim 1, wherein $R^1$ represents ethyl.

4. A salt of the compound according to claim 1.

5. A method of treatment and/or prophylaxis of a thrombotic event, comprising utilizing the compound according to claim 1, wherein the thrombotic event is a venous thromboembolism (VTE).

6. A method of treatment and/or prophylaxis of a stroke, cardiac infarction, atrial fibrillation and/or cardiac arrhythmia, comprising utilizing the compound according to claim 1.

7. A drug comprising at least one compound according to claim 1, having a prolonging effect on thrombin time, a thrombin inhibiting effect and/or an inhibiting effect on related serine proteases.

8. A drug comprising at least one compound according to claim 1 in combination with one or more inert, non-toxic, pharmaceutically suited excipients.

9. A drug comprising at least one compound according to claim 1 in combination with one or more further active agents.

10. A drug comprising at least one compound according to claim 1 for oral or parenteral administration.

11. The drug according to claim 7, wherein the drug is of enteric formulation.

12. A method for preparing the compound according to claim 1, comprising converting a nitrile of formula (A)

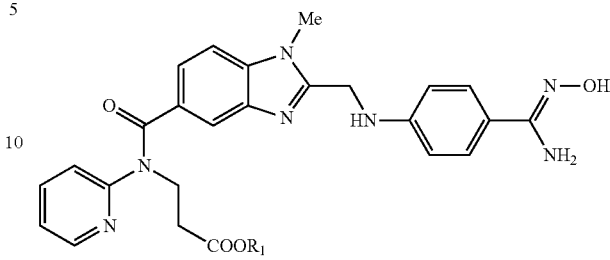

(A)

wherein $R_1$ represents hydrogen or a branched or unbranched, saturated or unsaturated, substituted or non-substituted hydrocarbon chain having a chain length of 1 to 12, into an amidoxime of formula (B)

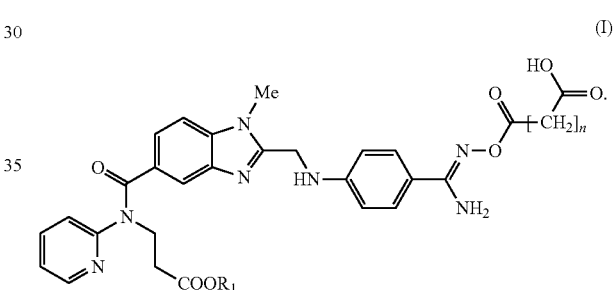

(B)

and reacting the amidoxime (B) with a dicarboxylic acid anhydride of formula (C)

(C)

wherein n represents 1-10, to yield the compound having formula (I):

(I)

* * * * *